United States Patent
Kern et al.

(10) Patent No.: US 7,725,174 B2
(45) Date of Patent: May 25, 2010

(54) DISTINGUISHING DIFFERENT DRUG EFFECTS FROM THE ELECTROENCEPHALOGRAM

(75) Inventors: Steven E. Kern, Salt Lake City, UT (US); Olinto Linares-Perdomo, Salt Lake City, UT (US); Santosh Kumar Balakrishnan, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 11/770,355

(22) Filed: Jun. 28, 2007

(65) Prior Publication Data

US 2008/0021345 A1    Jan. 24, 2008

Related U.S. Application Data

(60) Provisional application No. 60/817,029, filed on Jun. 28, 2006.

(51) Int. Cl.
    *A61B 5/04* (2006.01)
(52) U.S. Cl. .................................................. 600/544
(58) Field of Classification Search ................ 600/545
    See application file for complete search history.

(56) References Cited

U.S. PATENT DOCUMENTS

| 4,557,270 A * | 12/1985 | John ........................... 600/544 |
| 5,038,782 A * | 8/1991 | Gevins et al. ................ 600/383 |
| 7,089,927 B2 | 8/2006 | John et al. |
| 2002/0173729 A1 * | 11/2002 | Viertio-Oja et al. ......... 600/544 |
| 2003/0013981 A1 | 1/2003 | Gevins et al. |
| 2003/0119714 A1 * | 6/2003 | Naylor et al. .................. 514/1 |
| 2004/0122022 A1 * | 6/2004 | Gonzales et al. ....... 514/255.04 |
| 2006/0241562 A1 * | 10/2006 | John et al. .................. 604/503 |

FOREIGN PATENT DOCUMENTS

JP    2004115493 A  *  4/2004

OTHER PUBLICATIONS

Feshchenko, V., R. Veselis, and R. Reinsel, *Comparison of the EEG effects of Midazolam, Thiopental, and Propofol: the role of underlying oscillatory systems*. Neuropsychobiology, 1997; 35: p. 211-20.

Bischoff, P., E. Scharein, and G. Schmidt, *Topography of clonidine-induced electroencephalographic changes evaluated by principal component analysis*. Anesthesiology, 2000; 72: p. 1545-52.

Jahnig, P. and M. Jobert, *Methodological considerations for the evaluation of EEG mapping data: a practical example based on a placebo/diazepam crossover trial*. Neuropsychobiology, 1995; 31: p. 31-46.

(Continued)

*Primary Examiner*—Patricia C Mallari
(74) *Attorney, Agent, or Firm*—Foley & Lardner LLP

(57) ABSTRACT

This disclosure provides a method of indicating a subject's reaction to different agents administered to induce anesthesia. In particular, the subject's reaction can be assessed by receiving electrical signals from first and second electrodes spatially distributed on different regions of a subject's head, and by processing the electrical signals from the electrodes to provide a first indicator of the subject's reaction to a first of the agents and a second indicator of the subject's reaction to a second agent.

10 Claims, 10 Drawing Sheets

OTHER PUBLICATIONS

Theiler, J., *Efficient algorithm for estimating the correlation dimension from a set of discrete points*. Phys Rev A, 1987; 36(9): p. 4456-4462.

Ehlers, C., J. Havstad, A. Garfinkel, and D. Kupfer, *Nonlinear analysis of EEG sleep states*. Neuropsychopharmacology, 1991; 5: p. 167-76.

Preissl, H., W. Lutzenberger, F. Pulvermuller, and N. Birbaumer, *Fractal dimensions of short EEG time series in humans*. Neuroscience Letters, 1997; 225: p. 77-80.

Wackermann, J. and M. Matousek, *From the 'EEG age' to a rational scale of brain electric maturation*. Electroencephalography and clinical Neurophysiology; 1998; 107: p. 415-421.

Woyshville, M. and J. Calabrese, *Quantification of Occipital EEG Changes in Alzheimer's Disease Utilizing a New Metric: The Fractal Dimension*. Biol Phychiatry, 1994; 35: p. 381-387.

Yaylali, I., H. Kocak, and P. Jayakar, *Detection of seizures from small samples using nonlinear dynamic system theory*. IEEE Transactions of Biomed Eng., 1996; 43: p. 743-751.

Veselis, R., R. Reinsel, R. Alagesan, R. Heino, and R. Bedord, *The EEG as a Monitor of Midazolam Amnesia: Changes in Power and Topography as a Function of Amnesic State*. Anesthesiology, 1991; 74: p. 866-874.

Sleigh, J. and J. Donovan, *Comparison of bispectral index, 95% spectral edge frequency and approximate entropy of the EEG, with changes in heart rate variability during induction of general anaesthesia*. Br J Anaesthesia, 1999; 82: p. 666-671.

Grassberger, P. and I. Procaccia, *Measuring the Strangeness of Strange Attractors*. Physica, 1983; 9D: p. 189-208.

Pincus, S., I. Gladstone, and R. Ehrenkranz, *A regularity statistic for medical data analysis*. J Clin Monit, 1991; 7: p. 335-345.

Freeman, W. and J. Barrie, *Analysis of spatial patterns of phase in neocortical gamma EEGs in rabbit*. J Neurophysiol, 2000; 84: p. 1266-78.

Sebei, P., E. Lang, and I. Rampil, *A multicenter study of bispectral electroencephalogram analysis for monitoring anesthetic effect*. Anesth Analg, 1997; 84: p. 891-9.

Rampil, I., *A Primer for EEG Signal Processing in Anesthesia*. Anesthesiology, 1998; 89: p. 980-1002.

Ehlers, C., J. Havstad, A. Garfinkel, and D. Kupfer, *Nonlinear analysis of EEG sleep states*. Neuropsychopharmacology, 1991; 5: p. 167-76.

Theiler, J. and P. Rapp, *Re-examination of the evidence for low-dimensional, nonlinear structure in the human electroencephalogram*. Electroencephalogr Clin Neurophysiol, 1996; 98: p. 213-22.

Paulus, M., *Nonlinearity in normal human EEG: cycles, temporal asymmetry, nonstationarity and randomness, not chaos*. Biol Cybern, 1996; 75: p. 389-396.

Bullmore, E., M. Brammer, P. Bourlon, G. Alarcon, C. Polkey, R. Elwes, and C. Binnie, *Fractal analysis of electroencephalographic signals intracerebrally recorded during 35 epileptic seizures: evaluation of a new method for synoptic visualization of ictal events*. Electroencephalography and clinical Neurophysiology, 1994; 91: p. 337-345.

Bullock, T., M. McClune, J. Achimowicz, V. Iragui-Madoz, R. Duckrow, and S. Spencer, *Temporal fluctuations in coherence of brain waves*. Proc Natl Acad Sci, 1995; 92: p. 11568-11572.

Kaspar, F. and H. Schuster, *Easily calculable measure for the complexity of spatiotemporal patterns*. Phys Rev A, 1987; 36(2): p. 842-848.

Sandin, R., G. Enlund, P. Samuelsson, and C. Lennmarken, *Awareness during anaesthesia: a prospective case study*. The Lancet, 2000; 355: p. 707-711.

Knolle E., Oehmke M.J., Gustorff B., Hellwagner K., and Kress H.G., *Target-controlled infusion of propofol for fibreoptic intubation*. European Journal of Anesthesiology, 2003; 20: 565-569.

Egan TD. and Shafer SL., *Target-controlled infusions for intravenous anesthetics: surfing USA not!*, Anesthesiology, 2003; 99(5):1039-41.

Le Van Quyen M, Chavez M, Rudrauf D and Martinerie J. *Exploring the nonlinear dynamics of the brain*. J Physiol Paris, 2003; 97: 629-639.

Dikanev T, Smirnov D, Wennberg R., Velazquez JL and Bezruchko B., *EEG nonstationarity during intracranially recorded seizures: statistical and dynamical analysis*, Clinical Neurophysiology 2005; 116: p. 1796-1807.

Huang N.E., Shen Z., Long S.R., Wu M.L., Shih H.H., Zheng Q., Yen N.C. Tung C.C. and Liu H.H., *The Empirical Mode decomposition and Hilbert Spectrum for Nonlinear and non-stationary time series analysis*. Proc. R. Soc. Lond. A, 1998; 454: 903-995.

Huang Norden E., Shen Zheng, and Long Steven R., *A New View of Nonlinear Water Waves: The Hilbert Spectrum*. Annual Rev. Fluid Mech., 1999; 31: 417-457.

Nakata M, Mukawa J., and Fromm GH., *Evaluation of human consciousness level by means of "Automated Fluctuation Analysis" of high frequency electroencephalogram fitted by double Lorentzians*. Integr Physiol Behav Sci., 1993; 28: 343-352.

Rusalova, MN., *Frequency-Amplitude Characteristics of the EEG at Different Levels of Consciousness*. Neuroscience and Behavioral Physiology, 2006; 36(4): p. 351-358.

Gugino LD, Chabot RJ, Prichep LS, and John ER *Patient State Index (PSI) and arousal level during propofol induction in healthy adult volunteers* [Abstract]. Anesthesiology, 1998; 89(3A):U819-U819.

Bruhn J., Ropcke H., Rehberg B., Bouillon T., and Hoeft A., *Electroencephalogram Approximate Entropy Correctly Classifies the Occurrence of Burst Suppression Pattern as Increasing Anesthetic Drug Effect*. Anesthesiology, 2000; 93: p. 981-5.

Chen A., Herrmann C., *Perception of pain coincides with the spatial expansion of electronencephalographic dynamics in human subjects*. Neurosci Lett., 2001; 297(3): p. 183-6.

Cook, I., R. O'Hara, and H. Uijdehaage, *Assessing the accuracy of topographic EEG mapping for determining local brain function*. Electroenceph clin Neurophysiol, 1998; 107: p. 408-14.

Kochs, E., P. Bischoff, *Surgical Stimulation Induces Changes in Brain Electrical Activity during Isoflurane/Nitrous Oxide Anesthesia*. Anesthesiology, 1994; 80(5): p. 1026-1034.

Wolf, A., J. Swift, H. Swinney, and J. Vastano, *Determining Lyapunov exponents from a time series*. Physica, 1985; 16D: p. 285-317.

International Search Report and Written Opinion for PCT/US2007/072368 dated Aug. 21, 2008.

Prichep, L. S. et al., "The Patient State Index as an indicator of the level of hypnosis under general anaesthesia," British Journal of Anaesthesia, 92(3): p. 393-399, Epub Jan. 22, 2004.

\* cited by examiner

DISTINGUISHING DIFFERENT DRUG EFFECTS FROM THE ELECTROENCEPHALOGRAM

CROSS-REFERENCE TO RELATED APPLICATIONS

This application claims the benefit under 35 U.S.C. §119(e) of U.S. Provisional Patent Application No. 60/817,029, filed Jun. 28, 2006, which is herein incorporated by reference in its entirety.

STATEMENT REGARDING FEDERALLY SPONSORED RESEARCH OR DEVELOPMENT

The invention described within this disclosure was made with government support under Grant #DA018258 awarded by the National Institutes of Health. The Government has certain rights to this invention.

BACKGROUND

The present disclosure relates generally to the field of medicine and more particularly to the field of anesthesiology and the assessment of the effects of anesthetic drugs using an electroencephalogram (EEG).

Quantitative assessment of EEG data is used in basic and clinical research. The collection of simultaneous, multiple-channel EEG recordings allows one to be quickly overwhelmed by quantities of data from which rules and relationships can be difficult to sift. Consequently, much of the effort to evaluate this data has been directed towards determining global parameters from the EEG that can correlate with observations seen clinically for a number of normal and pathological conditions. However, the complexity of analysis of EEG data limits the use of EEG to monitor anesthesia.

There are 40 million surgical interventions performed annually in the U.S. under general anesthesia. The number of surgical and anesthesia-based interventions, both therapeutic and diagnostic, is expected to increase as the population ages. There is more than double that number worldwide. (See, EEG Processor Monitor Market Opportunities, Strategies, and Forecasts, 2003 to 2008. 2003, WinterGreen Research Inc.) Recent evidence from Sandin et al. gives credence to the need to monitor the complete anesthetic state. (See, Sandin, R., G. Enlund, P. Samuelsson, and C. Lennmarken, Awareness during anesthesia: a prospective case study. The Lancet, 2000. 355: p. 707-711.) In a prospective study of surgical patients, Sandin et al. showed an incidence of awareness during anesthesia of 0.1-0.2%. While most of the awareness incidents were benign, this still underscores the challenge faced by clinicians in administering drugs to depress the CNS.

There is a need for a system and method for determining the analgesic component to an anesthetic state of a patient. There is a need for a method to distinguish the amount of an analgesic and the amount of a sedative that contribute to an anesthetic state of a patient during surgical procedures. There is yet another need for a means to provide the output of the information collected from the method above to an attending anesthesiologist during a surgical procedure. Further still, there is a need for a pseudo-real time, direct computational method that does not rely on a database of empirical data which is drug-specific.

SUMMARY

According to one exemplary embodiment, a method of indicating a subject's reaction to different agents administered to induce anesthesia comprises receiving electrical signals from first and second sets of electrodes to be spatially distributed on different regions of a subject's head and processing the electrical signals from the electrodes to provide a first indicator of the subject's reaction to a first of the agents and a second indicator of the subject's reaction to a second agent.

According to another exemplary embodiment, a method is provided to distinguish the effects of different agents on electroencephalograms so that the relative contribution of each agent to a total physiological state and/or CNS function can be assessed. In particular, a method to characterize the interactions between agents used in anesthesia, for example, sedative/hypnotic agents and analgesics. More particularly, a method to quantitatively model the pharmacokinetic and/or pharmacodynamic interactions of sedative/hypnotic agents and analgesics. Assessment of the effects of different anesthetic components can provide guidance for anesthetic drug administration.

According to another exemplary embodiment, a method is provided for spatio-temporal monitoring of the EEG to assess the complete anesthetic state of a patient. Spatial differences in the EEG conducted with a subject can be correlated with the types and/or levels of different drugs administered to produce anesthesia. Processing of temporal and frontal EEG signals can be accomplished by linear and/or spectral frequency methods of analysis. Specifically, Approximate Entropy (ApEn) can be used as a non-linear index of anesthetic effect on the EEG. In a further embodiment, the Approximate Entropy (ApEn) method can be improved to speed up the processing time by judicious use of data segments to calculate the entropy measures.

DETAILED DESCRIPTION

Figure 1:
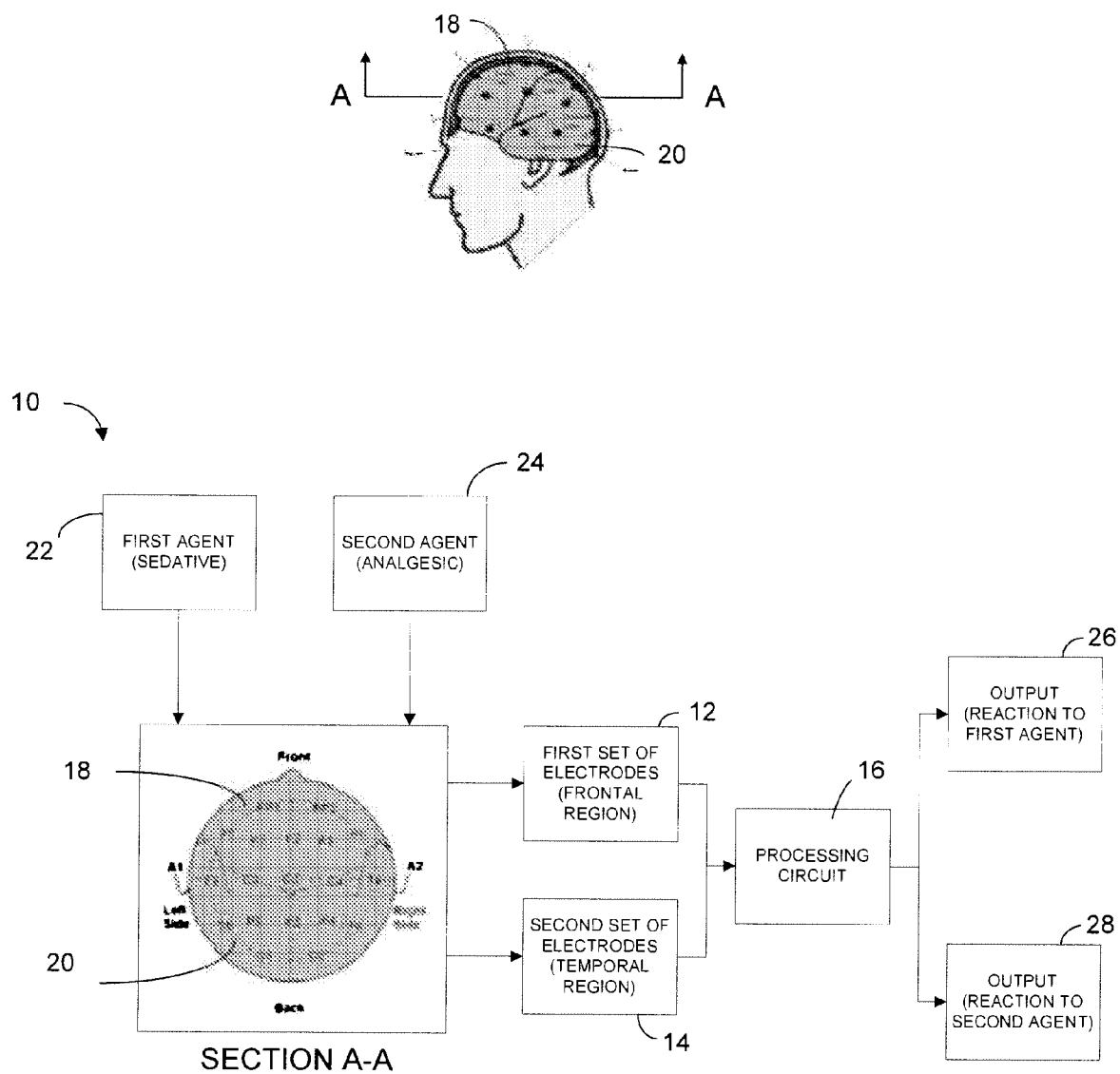
FIG. 1 is a block diagram of a system and method for indicating a subject's reaction to different agents administered to induce anesthesia, according to an exemplary embodiment.

Anesthesia is the condition of having the perception of pain and/or other sensations blocked. This allows patients to undergo surgery and other procedures without the distress and pain they would otherwise experience. Different anesthetic drugs can show different spatiotemporal EEG topologies even when administered to produce the same level of effect. Since different anesthetic agents work in different regions of the brain, this manifests as differences in surface EEG. See Feshchenko (See Feshchenko, V., R. Veselis, and R. Reinsel *Comparison of the EEG effects of midazolam, thiopental, and propofol: the role of underlying oscillatory systems.* Neuropsychobiol, 1997. 35: p. 211-20.). Using the spatial dimension of EEG signals, the global EEG signature can be deconvolved into components specific to anesthetic drugs, which in turn should also lead to specific neurophysiologic structures where those drugs are known or suspected to act. Bischoff et al. have shown that the topography of EEG changes from the $\alpha 2$ antagonist clonidine have a distinct pattern which differs from other anesthetic agents such as diazepam, which has been reported by Jahnig et al. (See Bischoff, P., E. Scharein, and G. Schmidt, *Topography of clonidine-induced electroencephalographic changes evaluated by principal component analysis.* Anesthesiology, 2000. 72: p. 1545-52; Jahnig, P. and M. Jobert *Methodological considerations for the evaluation of EEG mapping data: a practical example based on a placebo/diazepam crossover trial.* Neuropsychobiol, 1995. 31: p. 31-46.)

Since different sedatives and analgesics impact different subcortical structures in the brain, the reflection of those structures at the surface of the head are spatially dependent. Though the head can be thought of as a homogenous volume conductor that reflects all internal dipole sources to some projection to the surface, the ability to detect that reflection in the face of noise and other local subcortical currents is challenging. Given that cortical and subcortical circuits oscillate in patterns and frequencies that are often chaotic, non-linear methods that characterize these patterns may provide better information for sensing their transitions between changing CNS states. As is frequently observed during surgery, patients can change from an adequately anesthetized to an under-anesthetized state rapidly with a change in operative stimulus, just as a non-linear system transitions from one oscillating attractor to another.

Referring generally to the FIGURES, exemplary embodiments are illustrated of systems and methods to distinguish the effects of different agents on electroencephalograms so that the relative contribution of each agent to a total physiological state and/or CNS function can be assessed. A physiological state can be a state under normal or pathological conditions. "Agent" as used herein can mean a biologically active agent, a drug, a pharmaceutical composition, an inert substance, an organic compound, an inorganic compound, a chemotherapeutic, a statin, an antineoplastic, or any combination of the preceding chemicals. By assessment of the effects of the agents to a physiological state, mechanism of action of the agents to the CNS system, or the mechanisms of drug-drug interactions, may be deciphered.

In one exemplary embodiment, the interactions between agents used in anesthesia, for example, sedative/hypnotic agents such as propofol and analgesics such as remifentanil, may be characterized. More particularly, the embodiment quantitatively models the pharmacokinetic and/or pharmacodynamic interactions of sedative/hypnotic agents and analgesics.

Assessment of the effects of different anesthetics component can provide guidance for anesthetic drug administration or, in other words, an indicator of adequate anesthetic level or "depth" by which clinicians can titrate drug administration.

Anesthetic effects may be assessed in the EEG by determining spatial location on the scalp to assess effect coupled with signal processing methods to assess the raw EEG waveform. Assessment of each component to the anesthetic state may be achieved using analytical algorithms and physiologically-motivated knowledge regarding electrode location for measuring the complete anesthetic state.

In an exemplary embodiment illustrated in FIG. 1, a system 10 is provided for spatio-temporal monitoring of the EEG to assess the anesthetic state of a patient. Spatial differences in the EEG conducted by a subject can be correlated with the types and/or levels of different drugs administered to produce anesthesia. The subject may be either stimulated or not stimulated. Effects of anesthetics can be produced in real time, near real time or pseudo real time (e.g., within 6 to 10 seconds between receiving electrical signals and providing an indication), or non-real time, from multichannel EEG recordings through processing routines. It will be appreciated that where a specific EEG electrode is located and/or how the signals of the EEG are processed can be modified to visually reflect the physiological state of a brain. It has been identified that spatially distributed regions of the scalp can exhibit EEG changes unique to different drugs administered to the subject.

Referring again to FIG. 1, a first set of electrodes 12 are configured to be placed on or near a frontal region 18 of a subject's scalp. The subject may be any mammal, such as a human. A second set of electrodes 14 are configured to be located on or nor near the temporal region 20 of a subject's scalp. Electrodes 12, 14 may be electrical sensors configured to sense any of a variety of brain waves (e.g., delta, theta, alpha, sensorimotor rhythm or SMR, beta, gamma, etc.) and may be surface electrodes, indwelling electrodes, or optically or magnetically coupled sensors to detect changes in brain waves. For example, a Zip Prep® electrode manufactured by Aspect Medical Systems, Inc., Norwood Mass. may be used.

First and second electrodes 12, 14 may be spatially distributed on different regions of a patient's head. The hypothalamus is one region of the brain that typically gets depressed irrespective of whether the anesthetic is composed of a combination of agents or a single agent by itself. The spinal cord has many receptors for analgesics and so analgesics have a strong effect both in the spinal cord and in the brain. Animal experiments have shown if you separate the spinal cord from the brain, you can anesthetize them independently. When analgesics are taken, they impact or depress signals coming up to the brain from the body. These signals get reflected out in temporal areas more so than in frontal lobes. Thus, at least one set of electrodes may be placed on or near the temporal region or areas to better sense the effect on the subject of the analgesic. According to one exemplary embodiment, one set of electrodes is placed on the frontal region of the skull (forehead) and a second set of electrodes is placed on the temporal region (behind the dear) of a subject on the same side of the brain. These pairs of electrodes could be placed unilaterally or bilaterally on the head. In addition, other areas such as the parietal region or the region between the temporal and parietal zones could be used in conjunction with frontal placed electrodes to discern EEG effect. In various alternative embodiments, electrodes may be placed on or near any of the locations defined by the 10-20 system at F, T, C, P, and/or O locations, as illustrated in FIG. 1.

A first agent 22 (e.g., a sedative) is administered to the subject. A second agent 24 (e.g., an analgesic 24) is also administered to the subject. First agent 22 is administered to the subject for a different purpose than second agent 24 (e.g., sedation vs. analgesia vs. skeletal muscle relaxation), and the agents may comprise agents administered for other purposes. Analgesics may comprise one or more of morphine-like substances (e.g., morphine, codeine, hydrocodone, etc.), fentanyl derivatives (e.g., fentanyl, alfentanil, sufentanil, carfentanil, lofentanil, remifentanil, etc.), mixed agonist agents (e.g., nalbuphine, etc.), partial agonists (buprenorphine, butorphanol, etc.) and methadone. Sedatives may comprise one or more of propofol, etomidate, ketamine, inhalation anesthetics (e.g., isoflurane, sevoflurane, desflurane, halothane, etc.), benzodiazepines (e.g., midazolam, diazepam, lorazepam, etc.). Skeletal muscle relaxants may comprise one or more of succinylcholine, vecuronium, rocuronium, or cis-atracurium.

The reaction of the subject to the two different or independent agents is detected by the electrodes and analyzed in a processing circuit 16. The patient may react in a number of ways, including experiencing varying levels of sedation and/or ability to experience pain and/or ability to move muscles. The patient may also react by experiencing a change in the electrical signals in the brain. These electrical signals may change in any of a variety of ways, which changes may be reflected in the EEG. For example, with increasing amount of anesthetic agent, EEG signals tend to get higher in amplitude, lower in frequency, until a point where a portion of a window of the signal has no signal at all. Different agents may have this or other effects on the electrical signals of the brain.

In an exemplary embodiment, with electrodes 12 on a frontal region and electrodes 14 on a temporal region, the subject may react as follows. When an analgesic is administered, electrical signals detected by frontal electrodes 12 may not change appreciably until significant levels of analgesic are administered while electrical signals detected by temporal electrodes 14 may react by becoming more ordered with increasing magnitude and regularity. When a sedative is administered, electrical signals in frontal electrodes 12 may react similarly by becoming more ordered, and electrical signals from temporal electrodes 14 may not change as much until greater levels of sedative are administered. When both analgesic and sedative are administered, the effect can occur concurrently at both locations.

Processing circuit 16 is configured to receive electrical signals from electrodes 12, 14, process them using any of a plurality of algorithms, including those algorithms discussed below, and to provide output signals representing the electrical signals. Indications of the reaction of the subject to first agent 26 and second agent 28 are provided, for example, to the attending clinician or anesthesiologist. An indication of the reactions of the subject to the first agent 26 and the second agent 28 may be provided visually, audibly, etc., and may be represented in numerical and/or graph form on a commercially available EEG monitor, and can show historical data (e.g., a time profile) received from the electrodes for a determined time period (e.g. 30 minutes, one hour, etc.). The graph may be line, chart, bar, or any combination thereof and can be used by the anesthesiologist to determine the anesthetic state of the subject.

Processing circuit 16 may comprise digital and/or analog circuit components configured to receive electrical signals from electrodes 12, 14, to process those signals using the algorithms described herein and/or other algorithms (e.g., amplifying, digitizing or sampling, filtering with bandpass, lowpass, or highpass filters, storing, etc.), and to provide indications based on the processed signals or data. Circuit 16 may comprise one or more components of a known EEG monitor, such as a monitor manufactured by Aspect Medical Systems, Inc., Norwood Mass., wherein the existing EEG monitor is reconfigured with electrodes and software as described herein. Circuit 16 may comprise one or more microprocessors, microcontrollers, application-specific integrated circuits, memory, and other electronic components.

According to one advantageous aspect, indicators 26, 28 may represent the subject's reaction to the different agents independent of previous reactions of the subject to the different agents. Thus, indications may be provided continuously as a medical procedure progresses, providing an explicit, contemporaneous indicator of current state in absolute terms.

Figure 2:
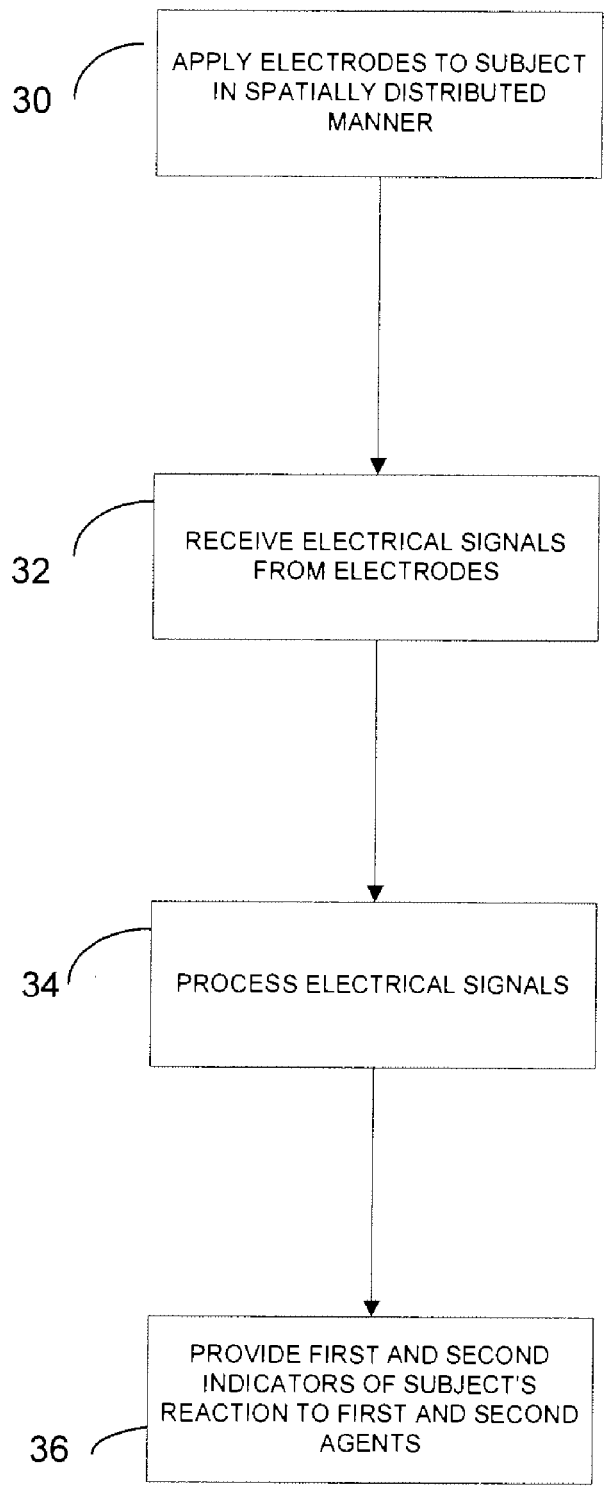
FIG. 2 is a flow diagram for a method of indicating a subject's reaction to different agents administered to induce anesthesia, according to an exemplary embodiment.
Figure 3:
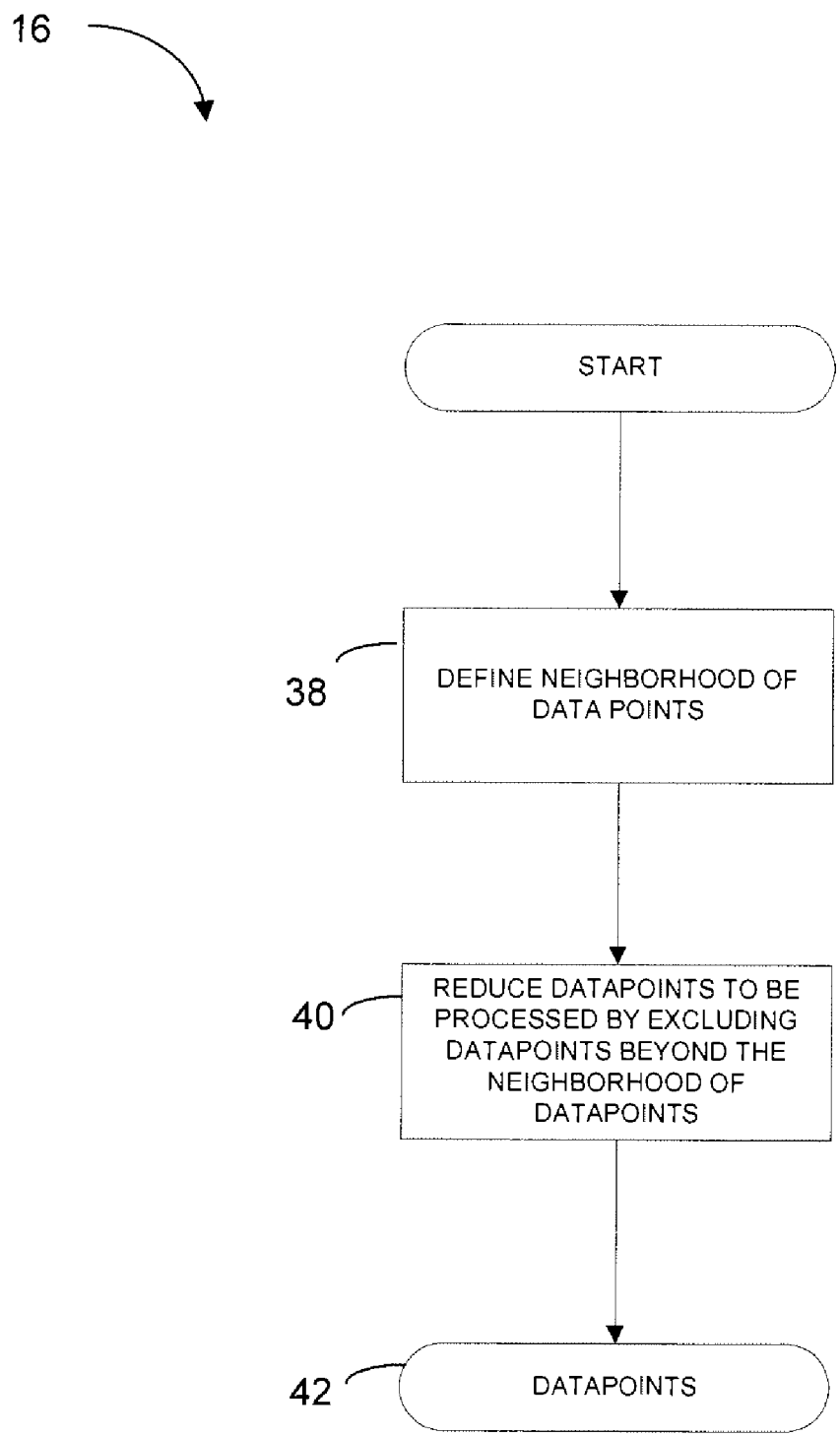
FIG. 3 is a flow diagram of a method for reducing data, according to an exemplary embodiment.

Referring now to FIGS. 2 and 3, exemplary methods of indicating a subject's reaction to different agents administered to induce anesthesia will be described. At step 30, electrodes are applied to a subject in a spatially distributed manner. For example, first electrodes 12 may be located in a frontal region of the subject's head and second electrodes 14 may be located in a parieto-temporal region of the subject's head. A plurality of different agents are administered to the subject having compositions for different purposes, for example, as a sedative, analgesic, skeletal muscle relaxant, etc. At step 32, processing circuit 16 is configured to receive electrical signals from electrodes 12 and 14. At step 34, processing circuit 16 is configured to process the electrical signals from the electrodes using any of a variety of signal processing techniques, which may include those described in greater detail below. At step 36, processing circuit 16 is configured to provide first and second indicators of the subject's reaction to the first and/or second agents.

According to one exemplary embodiment, processing circuit 16 is configured to apply a non-linear analysis method to at least the electrical signals from the first electrodes and/or second electrodes. The processing algorithms applied to electrical signals from first and second electrodes may be the same or different. The non-linear analysis method may comprise an approximate entropy (ApEn) method, an empirical mode decomposition (EMD) method, a Lyapunov exponent method, or other methods. Processing may further comprise steps performed before, during or in conjunction with other processing steps. Each of these methods, with exemplary variants, will be described in greater detail below.

Referring to FIG. 3, one exemplary pre-processing method to the ApEn method may comprise reducing the number of data points digitized from the electrical signals by (step 38) defining a neighborhood of data points and (step 40) reducing the number of data points to be processed by excluding datapoints beyond the neighborhood of data points from the ApEn method to (step 42) arrive at datapoints to be processed using the ApEn method. A neighborhood of data points is determined by a spatial grid placed over the data when plotted in the phase space. From a graphical point of view, if we distributed the attractor points in different boxes of same size, neighborhood points are referred to as those points inside the neighborhood boxes and inside adjacent boxes (including diagonally adjacent). For example, if all data points are plotted, and a 10 by 10 square grid is placed over the data points, a neighborhood may be defined as a single box and the eight adjacent boxes, thereby reducing the total number of data points to 9 boxes out of the total 100 boxes in the 10 by 10 square grid.

The ApEn algorithm is a function of three parameters: N, m and r. For N, the epoch length that indicates the length of the signal sample inside a moving window, is chosen to be 10 seconds. This selection is due because in exploring whether this method might have clinical utility for real time estimation in anesthesia or/and intensive care, we felt that a 10 second update interval for the indicator is reasonable. Other lengths are contemplated.

The parameter m determines how many previous estimates of ApEn are used to estimate the next estimate. It represents a type of signal smoothing where increasing m tends to damp fluctuations in ApEn values while increasing computational effort. The parameter may be fixed at a value of 2, or may alternatively be other values.

The parameter r, normally called signal filter factor, is the most sensitive parameter in the ApEn algorithm. The filter factor may be selected to be bigger than the noise in the time-series. In this work, where the objective is to find the best sensitivity result, the Pearson correlation factor between the anesthetic drug profile and the ApEn for different values of r is obtained. The greater the sensitivity, the higher the correlation factor. The best value obtained was r=0.1SD (Standard Deviation), though other values may be used.

According to one exemplary embodiment, a Datex monitor may have a spectral entropy and a state entropy indicator to look at EEG signals. The conventional Datex monitor looks at EEGs as well as other physiologic signals to come up with a multi-variable indicator of patient sedation state. The Datex monitor may be configured to operate an algorithm to provide an indicator of anesthetic state provided in pseudo-real time (e.g., within 6 to 10 seconds) reflective of the most recent 6 to 10 seconds of EEG signal being sensed. ApEn may be combined with the Theiler Box Method, developed by Jim Theiler, Physical Review A, 1987; 36:4456-4462. The ApEn method defines a neighborhood around a data point and determines how many other data points within a sample of data are within the neighborhood of R. A ratio of total data points within the neighborhood versus the rest of the data points outside the neighborhood is calculated, which provides information about whether the signal is small in amplitude or has a large, fluctuating amplitude, which provides part of the entropy calculation. The Theiler Box Method may be applied to reduce the data by excluding data points beyond the neighborhood of R. Data points outside the neighborhood of R are "grayer" than the number being looked for, so no calculations would be made based on data beyond the neighborhood of R. Instead, X data points within the neighborhood versus a total number of points may be determined to estimate the contribution of the entropy more expediently. While some precision may be lost, the algorithm may be sped up significantly.

As another example, processing circuit 16 may be configured to apply a Gaussianity indicator to data points digitized from the electrical signals to detect bursts in the electrical signals to provide further information to simplify the processing. Gaussianity is a statistical calculation that describes whether a signal has a normal Gaussian distribution in terms of its components or whether it has a supergaussian or sub-Gaussian distribution. With increasing amount of anesthetic agent, EEG signals tend to get higher in amplitude, lower in frequency, until a point where a portion of a window of the signal has no signal at all, followed by another portion still oscillating at high amplitude, relatively low frequency. As anesthesia is increased, the percentage of that window which essentially has little or no EEG activity starts to increase and the activity in the window that is left starts to develop intensity bursts. The bursts slowly go away with increasing anesthetic. Accordingly, processing circuit 16 can be configured to use Gaussianity to define when the burst condition occurs so that this information can be used in an informed way in the processing of the signals to avoid being misled by the bursts. Deep levels of anesthetic and burst suppression cause a dramatic change in Gaussianity, which can be used as an "on/off" indicator for processing of the EEG signals Processing may occur in the time and/or frequency domains. According to one advantageous embodiment, all processing is done in the time domain. Frequency domain analysis has been widely used because it is a convenient way to transform continuous signals into quantifiable parameters. However, two conditions important to Fourier analysis, stationarity and periodicity, are not met by EEG signals Processing of temporal EEG signals can be accomplished by linear, non-linear and/or spectral frequency methods of analysis. Non-linear analysis of EEG signals may utilize parameters based on regularity, stability and dimension which can be used to track states of CNS activity. (See, Ehlers, C., J. Havstad, A. Garfinkel, and D. Kupfer, Nonlinear analysis of EEG sleep states. Neuropsychopharmacology. Neuropsychopharmacology, 1991. 5: p. 167-76. Preissl, H., W. Lutzenberger, F. Pulvermuller, and N. Birbaumer, Fractal dimensions of short EEG time series in humans. Neurosci Lett, 1997. 225: p. 77-80. Wackermann, J. and M. Matousek, From the 'EEG age' to a rational scale of brain electric maturation. Electroencephalography and clinical Neurophysiology, 1998. 107: p. 415-421. Woyshville, M. and J. Calabrese, Quantification of Occipital EEG Changes in Alzheimer's Disease Utilizing a New Metric: The Fractal Dimension. Biol Phychiatry, 1994. 35: p. 381-387.) Since the EEG is a non-linear and perhaps non-stationary signal, methods which assess non-linear dynamics may provide useful information currently missing from assessment methods. (See Yaylali, I., H. Kocak, and P. Jayakar, *Detection of seizures from small samples using nonlinear dynamic system theory*. IEEE Trans Biomed Eng, 1996. 43: p. 743-51.)

Two groups have investigated the use of Approximate Entropy as a non-linear index of anesthetic effect on the EEG. (See Veselis, R., R. Reinsel, R. Alagesan, R. Heino, and R. Bedord, *The EEG as a Monitor of Midazolam Amnesia: Changes in Power and Topography as a Function of Amnesic State*. Anesthesiology, 1991. 74: p. 866-874; Sleigh, J. and J. Donovan, *Comparison of bispectral index, 95% spectral edge frequency and approximate entropy of the EEG, with changes in heart rate variability during induction of general anaesthesia*. Br J Anaesthesia, 1999. 82: p. 666-71.) Approximate Entropy (ApEn) is a regularity statistic modified from the Kolmogorov-Sinai Entropy indicator applied two decades before in EEG analysis. (See Grassberger, P. and I. Procaccia, *Measuring the Strangeness of Strange Attractors*. Physica, 1983. 9D: p. 189-20.) Approximate Entropy may determine the chaos in a time series of data, and may be used to relax some of the entropy restrictions. This reduces the data size and susceptibility to noise that make theoretical entropy indicators a less desirable option for real time applications. (See Pincus, S., I. Gladstone, and R. Ehrenkranz, *A regularity statistic for medical data analysis*. J Clin Monit, 1991. 7: p. 335-45.) In some exemplary embodiments, theoretical entropy indicators may be used. Approximately entropy may provide information from the EEG which can be used to assess CNS state during anesthesia. However, these methods are designed to determine qualities about the system which is generating the data and, as such, may be used to impart information about changes in CNS rather than just changes in the EEG. Information about the CNS can be related from a mesoscopic scale to a microscopic scale. (See, Freeman, W. and J. Barrie Analysis of spatial patterns of phase in neocortical gamma EEGs in rabbit. J Neurophysiol, 2000. 84: p. 1266-78.) While in some embodiments, these methods are computationally intense, (Preissl, H., W. Lutzenberger, F. Pulvermuller, and N. Birbaumer, Fractal dimensions of short EEG time series in humans. Neurosci Lett, 1997. 225: p. 77-80.) this issue can be addressed in alternative embodiments by speeding up the processing time by judicious use of data segments to calculate the entropy measures (e.g., the Theiler Box method or other methods). Though this has the potential to limit the accuracy of the entropy method in some embodiments, in other embodiments it provides a reasonable estimate that changes in correlation with signal complexity changes.

From the standpoint of applying these methods to determine relative changes in complexity of the EEG, estimates based on short series of data can produce reliable estimates that are useful in assessing epileptic events and distinguishing between different cognitive states in volunteers. (See Preissl, H., W. Lutzenberger, F. Pulvermuller, and N. Birbaumer, *Fractal dimensions of short EEG time series in humans*. Neurosci Lett, 1997. 225: p. 77-80; Yaylali, I., H. Kocak, and P. Jayakar, *Detection of seizures from small samples using nonlinear dynamic system theory*. IEEE Trans Biomed Eng, 1996. 43: p. 743-51.)

Processing of temporal EEG signals using various processing methods is exemplified in the EXAMPLES included herein below. A number of preliminary studies have been conducted to characterize the interaction between the two principle agents used in anesthesia, a first agent, a sedative/hypnotic and a second agent, an analgesic. Exemplary agents used in some studies include propofol as the sedative/hypnotic and remifentanil as the analgesic. These agents were chosen because they are prototypical of the many agents used within these classes, they are clinically popular, and they are pharmacokinetically evanescent, which allows them to be administered to volunteer subjects multiple times within a study period without significant accumulation of the drug. Any of a variety of other agents may be used.

EXAMPLE 1

Drug Interactions Between Sedative/Hypnotics and Opioids

Figure 4:
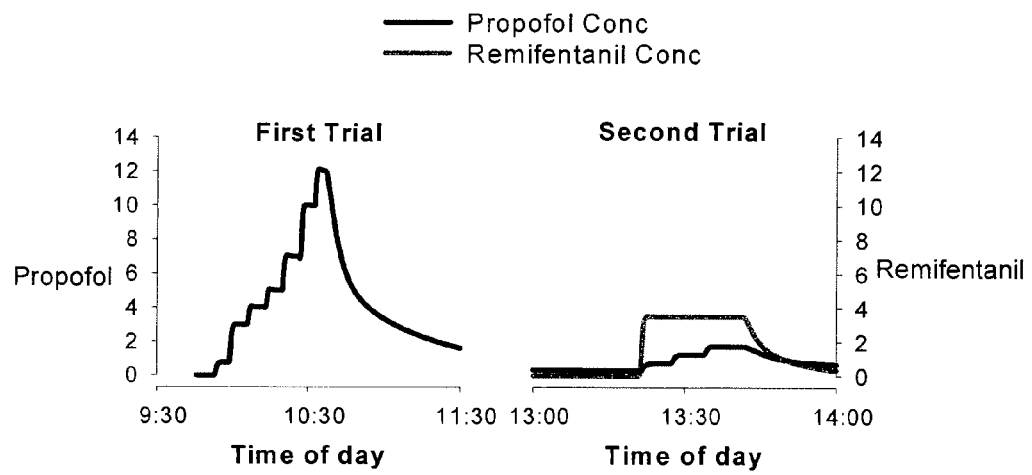
FIG. 4 contains line graphs illustrating two of the three target concentration profiles achieved in one study subject. At each target step, an assessment of drug effect is made. The target is increased until the subject no longer responds to laryngoscopy. The 6× decrease in propofol required to block the laryngoscopy response in the 2nd trial for this subject indicates the synergism between these two drugs for producing anesthesia. The trapezoidal curve of the second trial is remifentanil. The step-wise curve is propofol.

This study was designed to quantitatively model the pharmacokinetic and pharmacodynamic interaction of the sedative/hypnotic propofol with the analgesic remifentanil in human volunteer subjects. Using a computer controlled infusion pump, both agents were administered to the subjects at levels that initially produced light sedation and were eventually increased to produce full anesthesia. The computer controlled infusion pump uses a pharmacokinetic model to determine the delivery profile necessary to achieve and maintain a desired concentration of drug in the subject's bloodstream. This method of pharmacologic "concentration clamping" allows for rapid attainment of a desired concentration so that assessment of drug effect can occur under constant experimental conditions. At each targeted drug concentration, a series of tests of the subject were made to measure their responsiveness. Then the concentration was increased and the assessments were repeated, with the tests increasing in intensity. The concentration target ascended in a staircase fashion until the subject did not respond to laryngoscopy, a process used to prepare a subject for intubation. The study enrolled 24 subjects (12 male/12 female) who received three infusion trials during their experiment day. In their first infusion trial, the subjects received one of the agents alone. In the subsequent trials, the subjects received both agents together in combinations that spanned the normal range of use of these agents in clinical practice. An example of the drug concentration profile for two of the three trials from one subject is shown in FIG. 4.

Figure 5:
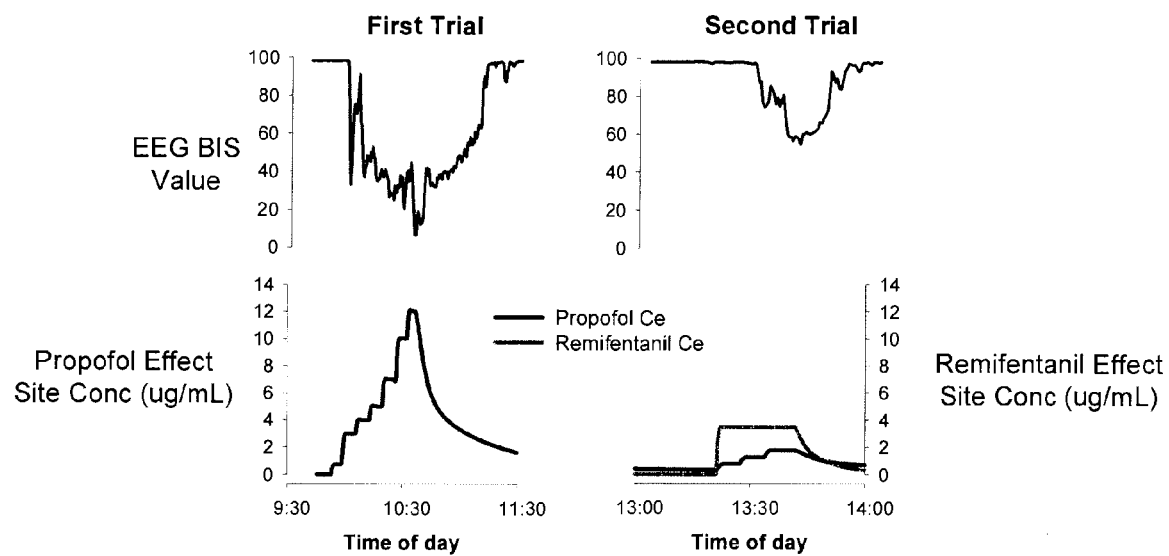
FIG. 5 contains line graphs illustrating changes in processed EEG (upper plots) with changes in anesthetic agents (lower plots) for the same subject illustrated in FIG. 4. The EEG parameter, rather than reflect the degree of anesthesia, reflects the sedative agent given. The trapezoidal curve of the second trial is remifentanil. The step-wise curve is propofol.

One result from this study was the impact combining these agents had on the processed EEG signal. In all subjects studied, the EEG was continuously measured with the Aspect A1000 EEG monitor (V 3.2, Aspect Medical Systems, Natick, Mass.). The monitor determines a processed EEG variable, the bispectral index (BIS), an empirically derived indicator which measures the depth of anaesthesia and facilitates anaesthetic titration. Unlike the surrogate measures used in the study, the BIS response did not indicate the synergism that occurred when the sedative and analgesic were combined. (BIS or bispectral index system is a uni-variant number from zero to 100 intended to tell the anesthesiologist a relative sedation state of the patient. BIS is calculated using a multi-parameter algorithm that combines a number of different components based on assessing the EEG, and in a piecewise, continuous way, it calculates the BIS index. One component is a database of previously collected anesthetic signals.) Instead, it tracked predominately the impact of the sedative on the EEG. This is apparent from the plots in FIG. 5. These plots show the change in BIS with increasing drug concentration levels for the same subject in FIG. 4. Instead of indicating anesthetic effect, the signal appears to indicate the relative amount of propofol given to the study subject without indicating the presence of the opioid analgesic at all. In fact, when the opioid is given alone to subjects, the BIS EEG shows very little change until such a significant amount of opioid is given that the subject is essentially obtunded. Similar results have been shown for this particular EEG indicator in clinical trials and research studies. (See, Sebel, P., E. Lang, and I. Rampil, A multicenter study of bispectral electroencephalogram analysis for monitoring anesthetic effect. Anesth Analg, 1997. 84: p. 891-9. Rampil, I., A Primer for EEG Signal Processing in Anesthesia. Anesthesiology, 1998. 89: p. 980-1002.)

EXAMPLE 2

Non-Linear Entropy Methods to Assess Temporal Changes in the EEG

The use of non-linear entropy methods was explored for assessing temporal changes in the EEG to determine other computational methods to produce the same results with respect to synergism between the two drugs. Review of the literature showed success with different non-linear entropy methods in reflecting other clinical changes in EEG state. (See, Ehlers, C., J. Havstad, A. Garfinkel, and D. Kupfer, Nonlinear analysis of EEG sleep states. Neuropsychopharmacology. Neuropsychopharmacology, 1991. 5: p. 167-76. Preissl, H., W. Lutzenberger, F. Pulvermuller, and N. Birbaumer, Fractal dimensions of short EEG time series in humans. Neurosci Lett, 1997. 225: p. 77-80. Yaylali, I., H. Kocak, and P. Jayakar, Detection of seizures from small samples using nonlinear dynamic system theory. IEEE Trans Biomed Eng, 1996. 43: p. 743-51. Theiler, J. and P. Rapp, Re-examination of the evidence for low-dimensional, nonlinear structure in the human electroencephalogram. Electroencephalogr Clin Neurophysiol, 1996. 98: p. 213-22. Paulus, M., Nonlinearity in normal human EEG: cycles, temporal asymmetry, nonstationarity and randomness, not chaos. Biol Cybern, 1996. Bullmore, E., M. Brammer, P. Bourlon, G. Alarcon, C. Polkey, R. Elwes, and C. Binnie, Fractal analysis of electroencephalographic signals intracerebrally recorded during 35 epileptic seizures: evaluation of a new method for synoptic visualization of ictal events. Electroencephalography and clinical Neurophysiology, 1994. 91: p. 337-345. Bullock, T., M. McClune, J. Achimowicz, V. Iragui-Madoz, R. Duckrow, and S. Spencer, Temporal fluctuations in coherence of brain waves. Proc Natl Acad Sci, 1995. 92: p. 11568-11572. Kaspar, F. and H. Schuster, Easily calculable measure for the complexity of spatiotemporal patterns. Phys Rev A, 1987. 36(2): p. 842-848.) This was in contrast to parameters derived from frequency analysis of the EEG (spectral edge frequency, median frequency), which have been shown to adequately track global changes in CNS state during anesthesia but lack the sensitivity to accurately track changes during light stages of sedation. (See, Sandin, R., G. Enlund, P. Samuelsson, and C. Lennmarken, Awareness during anaesthesia: a prospective case study. The Lancet, 2000. 355: p. 707-711.) A method was sought for analyzing changes in the EEG with time that would track the continuum from light sedation to full anesthesia. Finally, from experience with anesthetized patients during surgery, it often appears that they rapidly transition into and out of a state of anesthesia in a manner similar to shifts between attractor basins for non-linear dynamic systems. Thus, estimators based on these principles were assessed.

During the studies to model anesthetic drug interactions, the EEG was measured using the bifrontal montage required for calculation of the BIS parameter. This montage used electrodes placed at left and right frontal-mastoid locations (Fp1-Fpz, Fp2-Fpz) with a ground electrode placed at the center of the forehead. Raw EEG data was collected from both locations, low pass filtered (fc=48 Hz) and digitally sampled at 128 Hz. The digitized raw EEG signal was analyzed using three different non-linear indicators of signal entropy or regularity.

Approximate entropy (ApEn) was the first indicator that we evaluated. In this application, we were anticipating using it as an indicator of changing CNS "regularity" with increasing levels of sedation. ApEn has been referred to as a regularity statistic because it was derived without the inherent statistical assumptions upon which most entropy indicators are predicated. As such, its application with time series data for which the statistical properties are unknown is acceptable. (See, Pincus, S., I. Gladstone, and R. Ehrenkranz, A regularity statistic for medical data analysis. J Clin Monit, 1991. 7: p. 335-45.)

The basic idea behind ApEn is to choose a segment of data of length m and then evaluate whether this segment can be used to predict the behavior of a future segment of data of length m+1 within some acceptable error range, denoted as r. If a signal is highly regular, then the probability of predicting the new sequence is high. If the signal is irregular, then the probability of predicting a new sequence is low. The ApEn value represents the negative logarithm of this probability, therefore regular signals tend to have low ApEn values and irregular signals have higher ApEn values. The value of m, r and the number of samples over which to calculate ApEn (denoted as N), are empirically determined.

The selection of those values (N, m, r) may be done as follows:

a) N, the epoch length, is chosen to be 10 seconds. This selection of 10 seconds is based on its utility for real time application in anesthesia and intensive care.

b) m, the embedding dimension, is chosen to be 2 and the next dimension 3. This selection is based for real time application. Selection of high dimension produces closer results with the disadvantage in increased time consumption.

c) r, the filter factor parameter, is the most sensitive parameter in the entropy computation. It has been selected as a 0.1×SD, where SD is the standard deviation of the epoch length (N). The selection of 0.1SD was obtained used the correlation coefficient between the estimated anesthetic profile and the ApEn-entropy. The greater sensitivity, the higher the correlation factor, as shown in FIG. 14.

Figure 14:
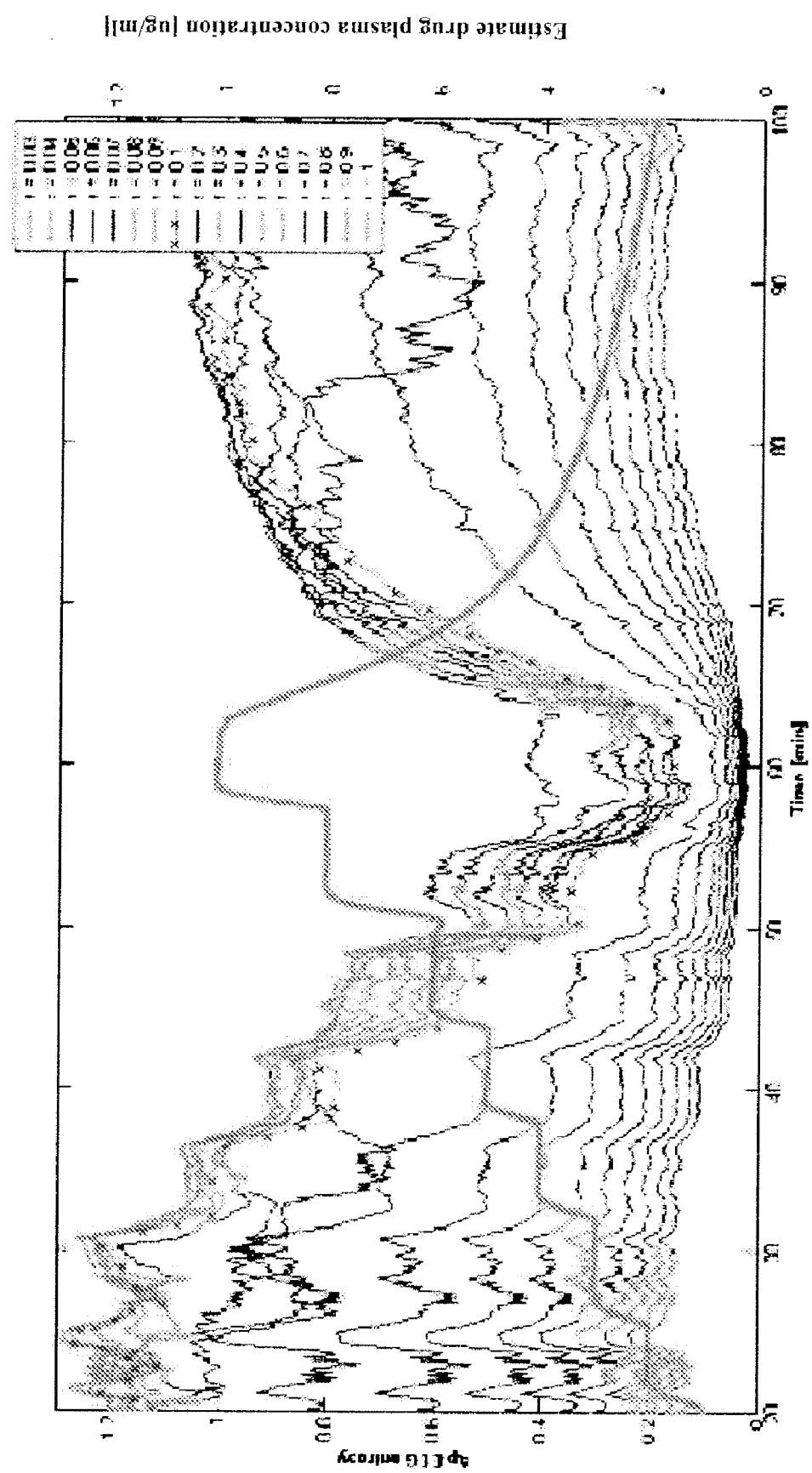
FIG. 14 is a chart showing entropy estimation for different r during anesthesia.

FIG. 14 is a chart showing entropy estimation for different r during anesthesia. The stair-step line rising to time 60 and thereafter falling represents the concentration of drug in the body of a patient. The remaining lines represent Ap-EEG entropy at different values of r, as shown in the table. Based on this empirical data, it was observed that a higher correlation factor is obtained when r=0.1SD.

Figure 6:
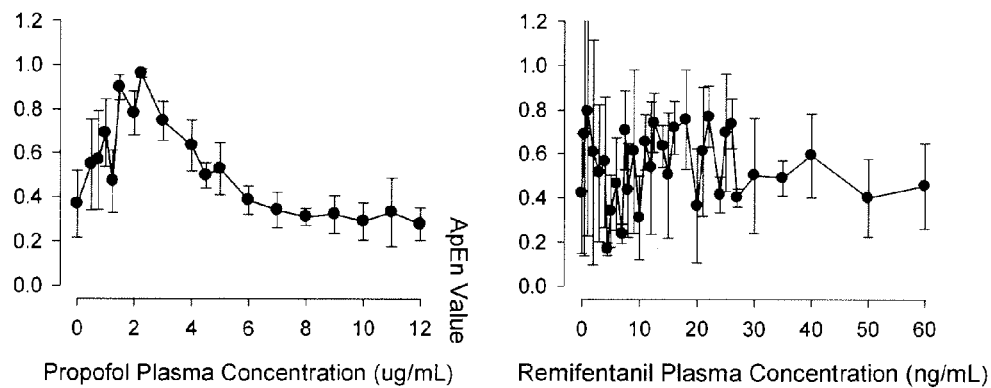
FIG. 6 contains line graphs illustrating changes in ApEn with drug concentration levels.

In applying ApEn to the EEG data from our drug interaction study, the operating hypothesis was that the EEG would show greater regularity with increasing drug concentration and CNS depression. In general, the results showed that ApEn decreased with sedation created by the sedative/hypnotic propofol. When the data from subjects who received remifentanil was analyzed, the results were similar to those seen with the BIS. There was relatively little change in ApEn for subjects who received remifentanil until the concentration administered was significantly greater than is typically used in clinical anesthesia. The average change in ApEn with propofol and remifentanil in study subjects is shown below in FIG. 6. In the first chart, artifacts were created by the patient moving around for concentrations up to approximately 2, and then the ApEn value begins to fall off monotonically after that, once the patient was quiescent. This consistency between the empirically derived BIS and the computationally derived ApEn with respect to EEG change in subjects who received remifentanil prompted us to consider spatial distribution of EEG signals as a rationale for the lack of information present in the EEG when the opioid was given. In the second chart on the right in FIG. 6, no clear pattern emerged.

Though both sedatives and opioids have effect in thalamic relay networks of the brain, their projection of CNS effects to the brain surface predominate in different cortical regions. (See, Feshchenko, V., R. Veselis, and R. Reinsel Comparison of the EEG effects of midazolam, thiopental, and propofol: the role of underlying oscillatory systems. Neuropsychobiol, 1997. 35: p. 211-20.) All anesthetic agents have a significant impact on frontal regions of the cerebral cortex as their concentration in a subject is increased. In contrast, opioids tend to show cortical effects in temporal regions of the CNS. Since the bifrontal montage location of the electrodes required for measurement of BIS is located frontally, it is likely that the location precludes the ability to "see" effect of the opioid on the electrodes until significant global CNS depression occurs.

EXAMPLE 3

Figure 7:
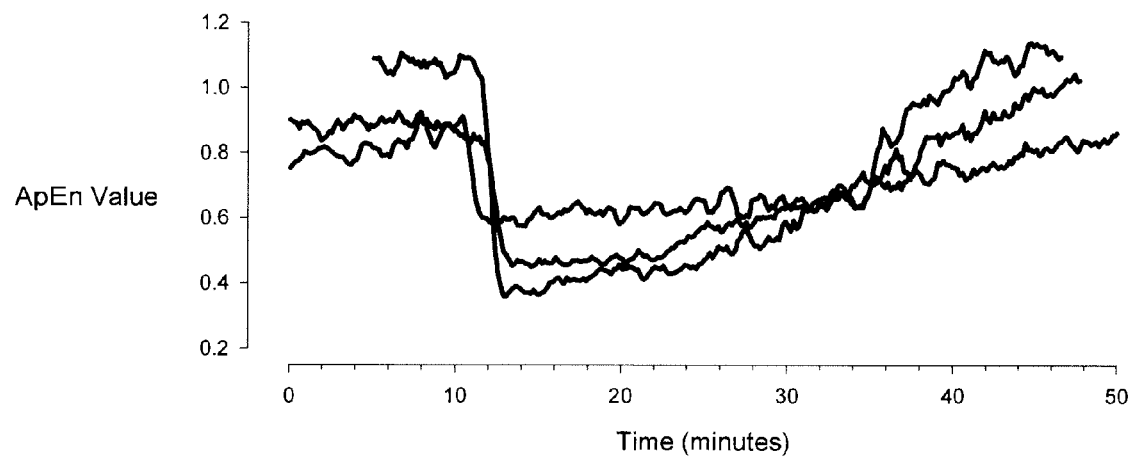
FIG. 7 is a line graph illustrating EEG Approximate Entropy calculated from temporal electrodes in three swine that received a 10 minute infusion of remifentanil combined with a low level of inhalation anesthetic in the background (0.2 MAC or minimum alveolar concentration). ApEn changes detectably with increasing opioid when temporal electrode locations are used.

To test this theory, EEG data was evaluated that was gathered in another study to assess the impact of a 10 minute infusion of remifentanil in swine. This study used a montage that covered the temporal region as well as frontal zones. When this data was analyzed using ApEn, all animals evaluated showed a significant decrease in ApEn levels with increasing concentration of remifentanil. This gave evidence to the idea that electrode location was related to assessing the impact of different sedative/hypnotic and opioid analgesic drugs. Since the opioid's effect is reflected in a region of the cortex that is far away from the location of the frontal electrodes needed for BIS, it is likely that these frontal electrodes do not "see" the impact of the opioid on the EEG until significant CNS depression occurs. The results of this analysis are shown in FIG. 7. FIG. 7 is a line graph illustrating EEG ApEn calculated from temporal electrodes in three swine that received a 10 minute infusion of remifentanil combined with a low level of inhalation anesthetic in the background (0.2 MAC or minimum alveolar concentration). ApEn changes dramatically with increasing opioid when temporal electrode locations are used. This finding confirmed that the lack of impact of the analgesic on the processed EEG was a function of where on the scalp it was measured rather than how it was processed and furthered our interest in developing new methods to assess both the sedative/hypnotic and the analgesic components of an anesthetized state, independently if possible.

EXAMPLE 4

In this study, four pigs were administered anesthetics. Two animals were administered propofol, then allowed to recover, then given remifentanil and allowed to recover. Recovery was determined by looking at the EEG signal in real time and seeing when it went from a state that appeared to be changed or depressed back to a regular state. Data was collected and processed off-line.

We then administered to two pigs a first agent followed by a second agent followed by both agents and to the other two pigs the second agent followed by the first agent followed by the combination of agents. The first agent was propofol and the second agent was remifentanil. We looked at the changes in the EEG on four different electrode locations and saw that there were different patterns that emerged from those locations depending on whether we were giving the first agent or second agent. This data can be useful in trying to identify the relative contribution of those two components to the total anesthetic state.

EXAMPLE 5

EEG Analysis with Other Non-Linear Indicators

Figure 8:
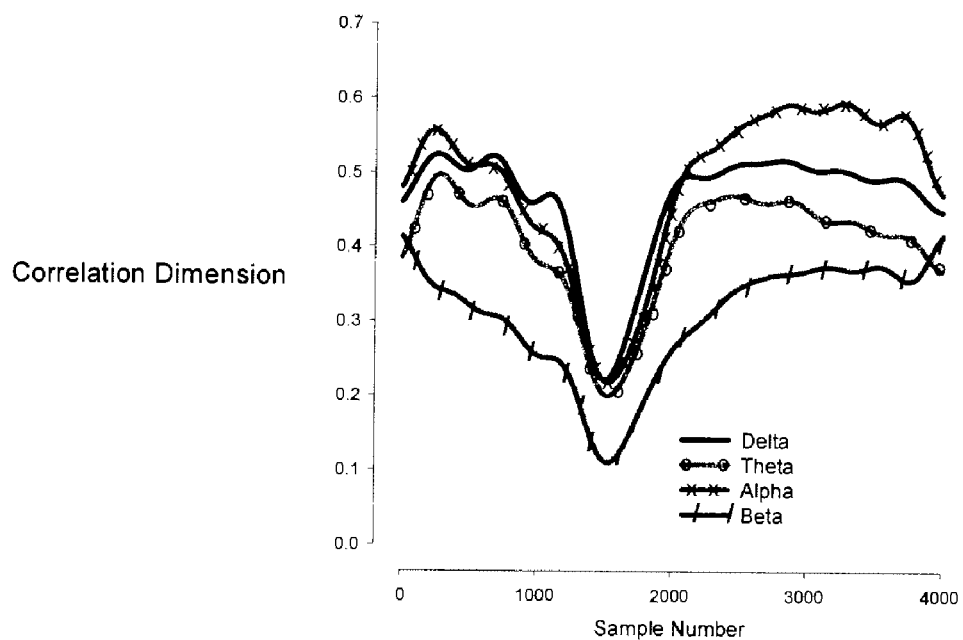
FIG. 8 is a line graph illustrating change in correlation dimension with changes in propofol concentration for one study subject. The change for each separate clinical frequency band is shown.

To further assess the ability of non-linear indicators to provide good indicators of drug effect from the EEG, we have applied correlation dimension and estimation of Lyapunov exponents to EEG signals collected from subjects in the study who received the sedative propofol. As with ApEn, these entropy measures compare changes in the time series of raw EEG data as it is generated. However, they are designed to determine qualities about the system which is generating the data. As such, they have potential to impart information about changes in CNS rather than just changes in the EEG. Information can be related about the CNS from a mesoscopic scale to a microscopic scale. (See, Freeman, W. and J. Barrie Analysis of spatial patterns of phase in neocortical gamma EEGs in rabbit. J Neurophysiol, 2000. 84: p. 1266-78.). An example from this preliminary analysis with correlation dimension is shown in FIG. 8. Correlation dimension has not been used for real time analyses in the past because the computation usually requires large data sets for precise determination of the actual dimension of the data space. (See, Preissl, H., W. Lutzenberger, F. Pulvermuller, and N. Birbaumer, Fractal dimensions of short EEG time series in humans. Neurosci Lett, 1997. 225: p. 77-80.) To address this problem, we used short segments (e.g., 10 seconds) of data to calculate the correlation dimension and averaged the critical distance parameter $\epsilon$, with each new estimate. Though this limits the accuracy with which signal dimension can be determined, it provides a reasonable estimate that changes as signal complexity changes. These results show the change in EEG complexity as a subject transitions from awake to deeper levels of sedation. Separating the EEG signal into clinical frequency bands ($\delta$, $\theta$, $\alpha$, $\beta$), changes in correlation dimension appear in the higher frequency ranges first.

Figure 9:
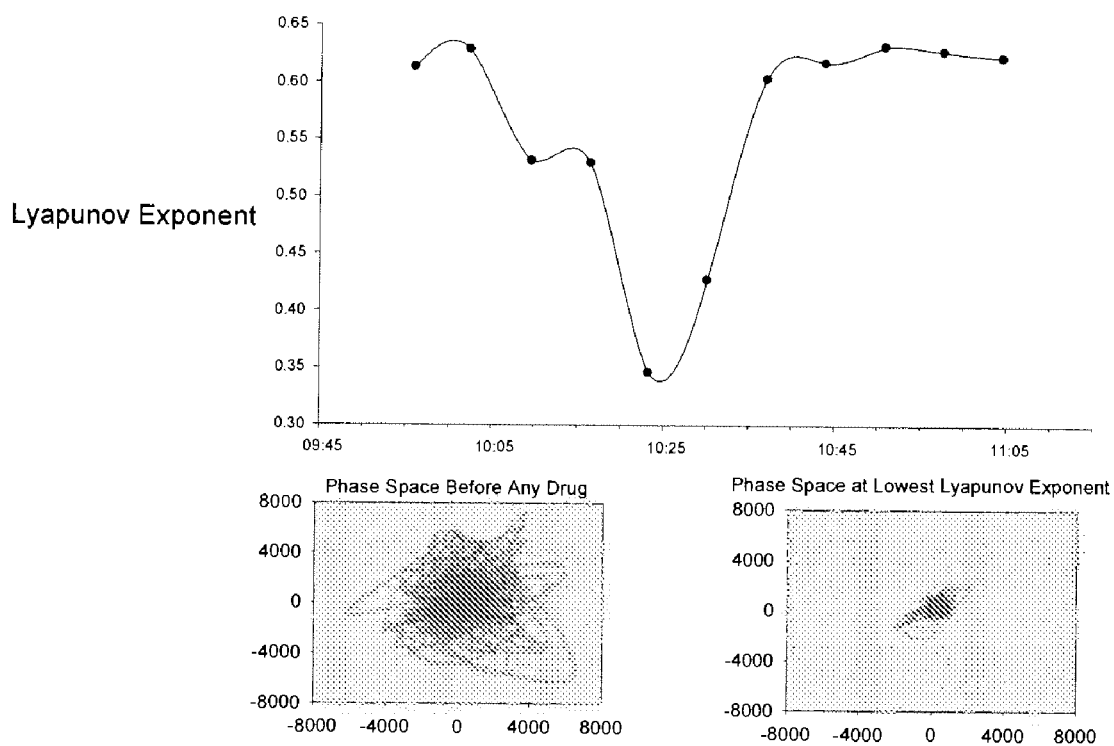
FIG. 9 illustrates Lyapunov Exponent and raw EEG signal phase diagrams for a subject receiving sedation with propofol. With increasing sedation, the exponent tends towards a positive value indicating stability. The area encompassed by the phase space also contracts. The phase information provides an additional dimension for assessing EEG complexity.

Using the same raw EEG data, Lyapunov exponents of the EEG were also determined. Lyapunov exponents provide a qualitative indicator of signal stability. Unstable signals are sensitive to initial conditions and thus the predictability of their future trajectory is difficult. With increasing sedation level, the EEG becomes less unstable and chaotic relative to its condition in the awake subject. Lyapunov exponent characterizes this level of stability and provides information in both time and phase space of the signal. (See, Wolf, A., J. Swift, H. Swinney, and J. Vastano, Determining Lyapunov exponents from a time series. Physica, 1985. 16D: p. 285-317.) An example from a different subject of the change in Lyapunov exponent and signal phase space with increasing sedative level is shown in FIG. 9.

Following is a discussion regarding the Empirical Mode Decomposition (EMD) and fourth moment statistic analysis. This method estimates the plasma effect site concentration from the electroencephalogram.

Different anesthetic agents are used to induce a state of unconsciousness in the operating room (OR), for managing post-operative pain and in the intensive care unit (ICU). The plasma effect site concentration of the drugs used or an estimate thereof is a useful measure for controlling level of anesthetic administration. A surrogate measure of plasma effect site concentration may be provided using an electroencephalogram (EEG) time series.

EXAMPLE 6

The utility of empirical mode decomposition (EMD) and fourth-moment statistical analysis of the EEG during target-controlled infusion (TCI) of propofol in healthy human volunteers was investigated. After institutional approval, twelve healthy volunteers, ages 18-41 (mean 26) years, who were in good physical condition, were enrolled. Propofol was administered using an infusion pump programmed with corresponding pharmacokinetic parameters. The drug concentration produced by the kinetic infusion in the subject was sequentially increased until they tolerated laryngoscopy. The raw EEG was recorded continuously, using an A-1000 EEG monitor (Aspect Medical, Inc., Natick, Mass.), with a bipolar montage Fp2-Fpz, Fp1-Fpz (international 10-20 system of electrode placement) and sampled at 128 Hz. Empirical mode decomposition was performed to separate the intrinsic mode functions (IMFs) of the EEG time series. Fourth-moment statistical analysis was performed on the first IMF, which corresponds to the high frequency component of the EEG. This measure was correlated with the estimated plasma effect site concentration obtained from infusion pump, using Pearson's correlation coefficient.

Changes in the gaussianity, quantified using fourth-moment statistic, of the first IMF during infusion of propofol showed high correlation with the estimated plasma effect site concentration obtained from the infusion pump. This was evidenced by a Pearson's correlation co-efficient of $\rho > 8.7$).

Empirical mode decomposition and fourth-moment statistic analysis can be used to derive a surrogate measure of the plasma effect site concentration from the EEG during infusion of propofol in humans. This non-invasive technique may be used for monitoring and controlling anesthetic administration in the operating room and intensive care unit.

Target-controlled infusion (TCI) systems report a predicted concentration for the drug of interest. (See Knolle E., Oehmke M. J., Gustorff B., Hellwagner K., and Kress H. G., Target-controlled infusion of propofol for fibreoptic intubation. European Journal of Anesthesiology, 2003. 20:565-569.) Because the TCI system predicts the concentration on the basis of the drug's typical pharmacokinetic behavior (i.e., population pharmacokinetics), there is always a discrepancy between the predicted concentration and the actual concentration in the individual patient. In other words, the predicted concentration is only an estimate. (See Egan T D., and Shafer S L., Target-controlled infusions for intravenous anesthetics: surfing USA not!, Anesthesiology, 2003, 99(5): 1039-41.) Anesthetic administration has a corresponding effect on the physiological state of the body. Therefore, physiological signals collected from the body during drug infusion could be used as a surrogate measure of the plasma drug concentration. One of these physiological signals could be the EEG, normally collected during drug infusion. However, the complicated neural behavior of the brain manifests itself in a non-linear and non-stationary on the electro-encephalogram (EEG) signal. (See Le Van Ouyen M, Chavez M, Rudrauf D and Martinerie J. Exploring the nonlinear dynamics of the brain. J Physiol Paris. 2003, 97: 629-639; Dikanew T, Smirnov D, Wennberg R., Velazquez J L and Bezruchko B. EEG nonstationarity during intracranially recorded seizures: statistical and dynamical analysis.)

It may be possible to obtain a surrogate measure of the plasma effect site concentration, of the anesthetic drug delivered, from the EEG time series using specific mathematical tools for non-linear and non-stationary time series.

In this work, the empirical mode decomposition (EMD) or Huang Transform method was used as a tool to overcome the restrictions imposed by assumptions of linearity and stationarity usually made during time-series analysis (See Huang N. E., Shen Z., Long S. R., Wu M. L., Shih H. H., Zheng Q., Yen N. C. Tung C. C. and Liu H. H., The Empirical Mode decomposition and Hilbert Spectrum for Nonlinear and Nonstationary time series analysis. Proc. R. Spc. Lon. A. 1998, 454: 903-995; Huang Norden E., Shen Zheng, and Long Steven R., A NEW VIEW OF NONLINEAR WATER WAVES: The Hilbert Spectrum. Annual review of Fluid Mechanics, 1999, 31: 417-457.). In the EMD method, any time series, linear or non-linear, stationary or not stationary, has intrinsic modes of oscillation called intrinsic mode functions (IMFs). Where the IMFs are generated being sorted in descending order of frequency, where the IMF1 is associated with the locally highest frequency of the original data. In various alternative embodiments, the Huang Transform may be used to analyze sedative, analgesic, or other components of anesthesia.

Since previous research has shown that the high frequency components of the EEG are related to consciousness (See Nakata M, Mukawa J. and Fromm G H. Evaluation of human consciousness level by means of "Automated Fluctuation Analysis" of high frequency electroencephalogram fitted by double Lorentzians. Integr Physiol Behav Sci. 1993, 28: 343-352.) in this work we explored changes in characteristics of the Intrinsic Mode Function-high frequency component (IMF1) with increasing anesthesia. In particular, we studied the changes in gaussianity of the IMF1 using fourth moment statistical analysis for use as a surrogate measure of the actual plasma drug concentration. For comparison purposes, we correlated the surrogate measure of the plasma drug concentration with the estimate plasma effect site concentration obtained from the infusion pump using Pearson's correlation coefficient.

The EEG data used in this work was collected as part of a project to characterize pharmacokinetic and pharmacodynamic drug interactions. We obtained written informed consent from 12 subjects (ages 18-41, mean 26 years), all of whom were in good physical condition. Each randomly selected subject received doses of propofol targeted to achieve increasing concentration levels until the subject would tolerate laryngoscopy. The drug was administered using an infusion pump that was programmed with pharmacokinetic parameters specific to the agent being delivered. This allowed the pump to maintain the concentration of drug in the subject's bloodstream and at the site of drug effect at a constant level. Beginning with a sub-therapeutic concentration target for each subject, the targeted concentration of Propofol was increased in steps. At each target step, the subject was evaluated for responsiveness to multiple stimuli, which assessed the subject's state of consciousness and response to pain. These stimuli included tibial pressure algometry, electrically induced pain, response to laryngoscopy, and assessment with a verbal sedation scale. Arterial blood samples were obtained at each target concentration step as well. The maximum level of propofol was determined when the subject no longer responded to the most noxious stimulus, the placement of a laryngoscope in the airway. At that point, the computer-controlled infusion was discontinued and the subject was allowed to recover from anesthetic administration.

The EEG was recorded continuously with a bipolar montage configured in the frontal area based on the international 10-20 system of electrode placement (Fp1-Fpz, Fp2-Fpz).

The raw EEG was sampled at 128 Hz and low-pass filtered at 48 Hz. EEG recordings were performed with an A-1000 EEG monitor (Aspect Medical Inc, Natick Mass.). The raw EEG, the estimated plasma effect site concentration, obtained from the infusion pump, and the Signal Quality Index (SQI) were stored on a computer hard disk for further offline analysis. Electrode impedance was kept below 5 kΩ. In addition, heart rate, blood pressure, respiratory rate, and oxygen saturation level were measured during the drug infusion process. Stimuli to assess subject's responsiveness were administered at each concentration plateau maintained by the pharmacokinetic infusions.

In Empirical Mode Decomposition (EMD), the data decomposition is based on the assumption that any time-series consists of different simple intrinsic modes of oscillation know as Intrinsic Mode Functions (IMFs) imbedded in the data. The EMD may comprise an adaptive time-frequency analysis, meaning that its basic functions are derived adaptively from the data. An Intrinsic Mode Function (an oscillatory mode) satisfies two conditions:

A. In the hold data set, the number of extrema (maximum and minimum) and the number of zero-crossing must be equal or differ at most by one.

B. At any point, the mean value of the envelope defined by the local maxima and the envelope defined by the local minima is zero.

An important characteristic of the IMF components is that they have physical meaning, that means that any IMF represents a specific physical phenomena underlying the system.

A systematic way to extract the IMFs from the data is through six steps:

1. Identification of all the extrema (maxima and minima) of the data in analysis.
2. Connect all the local maxima, and all the local minima, via cubic spline interpolation to generate the upper and lower envelope.
3. Obtain the local mean from the upper and lower envelope.
4. Obtain the IMF-candidate for the subtraction of the mean from the data.
5. Check the properties (a and b) of the IMF-candidate obtained.
    A. If the IMF-candidate is not an IMF, replace the original data with the IMF-candidate and repeat the procedure from step 1.
    B. If the IMF-candidate satisfied the properties, evaluate the residue as the original data-IMF.
6. Repeat the procedure from step 1 to 5 by sifting the residual signal.

A criterion to stop the extraction of the IMFs is needed so that the resulting IMF components retain enough physical meaning from the electroencephalographic time-series. This can be obtained by limiting the size of the standard deviation computed from the two consecutive sifting results as indicated below.

$$SD = \sum_{i=1}^{N}\left[\frac{|h_{(k-1)}(i) - h_k(i)|^2}{h_{(k-1)}^2(i)}\right]$$

Where: N=number of points in the segment, k=the sifting number, and h=the IMF candidate and SD the standard deviation.

To stop the sifting process, a typical value of SD is selected between 02.-0.3. The above procedure results in the original data decomposition into n-empirical mode of oscillations (n is a function of the original data) and a residue r(t), which can be either a monotonic function or a single cycle of oscillation.

A criterion to stop is needed so that the resulting IMF components retain enough physical sense of both amplitude and frequency modulation. The sifting process is stopped when all interesting intrinsic modes of the original series have been extracted; we checked the range of the residue r and the sifting process ends when the range of the r is less that a predefined value respects to the original signal. The predefined value to stop the sifting process used in this works was at <0.5% of the original time series.

Finally, the original signal can be exactly reconstructed by linear superposition of the IMFs and the residual. (1).

$$\text{original\_data} = \sum_{i=1} IMF_i + r \qquad (1)$$

The above procedure results in a decomposition of the data into n-empirical mode of oscillations (n is a function of the data) and a residue r(t), which can be either a monotonic function or s single cycle of oscillation, where r=residue, IMF=Intrinsic Mode Function, n, the number of modes of oscillation, is a function of the data in analysis and the stopping criterion used.

Several characteristics are important from the IMFs obtained using the EMD. One is that any IMF has a physical meaning. Another is that an IMF has a unique local frequency, and another is that different IMFs do not exhibit the same frequency at the same time.

In the present works the EMD method was programmed in MATLAB professional 7.

The fourth-moment statistic measure (Kurtosis) (2) is a quantification of gaussianity of a time series. Kurtosis is a measure of how outlier-prone a distribution is in nature. The Kurtosis of the normal distribution is 3 and defined as Gaussian distribution. Distributions that are more outlier-prone than the normal distribution have Kurtosis greater than 3 and are defined as super-gaussian distribution. Distributions that are less outlier-prone have Kurtosis less than 3 and defined as sub-gaussian distribution.

Some definitions of Kurtosis subtract 3 from the computed value such that the normal distribution has Kurtosis of 0, super-gaussian distribution has Kurtosis greater that zero and sub-gaussian distribution has Kurtosis lower than zero.

$$\text{Kurtosis} = \frac{\sum_{i=1}^{N}(Y_i - \overline{Y})^4}{((N-1)(std)^4)} \qquad (2)$$

Here $\overline{Y}$ is the mean, std is the standard deviation, and N is the number of data points.

The electroencephalogram time-series was divided into epochs of 10-s duration (1280 samples) and passed through the EMD method to obtain the IMFs as discussed below. Fourth-moment statistic analysis was computed in the IMF high frequency component and passed through a smoothing filter. The time window was used without overlapping. The EMD-Kurtosis results were correlated, using the Pearson correlation factor (3), with the estimate plasma effect site concentration obtained from the infusion pump. Only EEG time-series with a signal quality index (SQI) bigger that 50 was considered.

$$CorrFac = \frac{\sum_{i=1}^{n}(x_i - \overline{x_i})(y_i - \overline{y_i})}{\sqrt{\Sigma(x_i - \overline{x_i})^2}\sqrt{\Sigma(y_i - \overline{y_i})^2}} \quad (3)$$

where $\overline{y}$ and $\overline{x}$ are the mean values, and $x_i$ and $y_i$ are the series to be correlated. N is the number of data points in the epoch.

The EEG time series obtained from 11 subjects from a group of 12 were decomposed in their IMFs using EMD. The number of the oscillatory modes extracted was 7. One subject was not considered on the analysis because it presented a poor signal quality index (SQI) below 50 during all infusion time.

Figure 10:
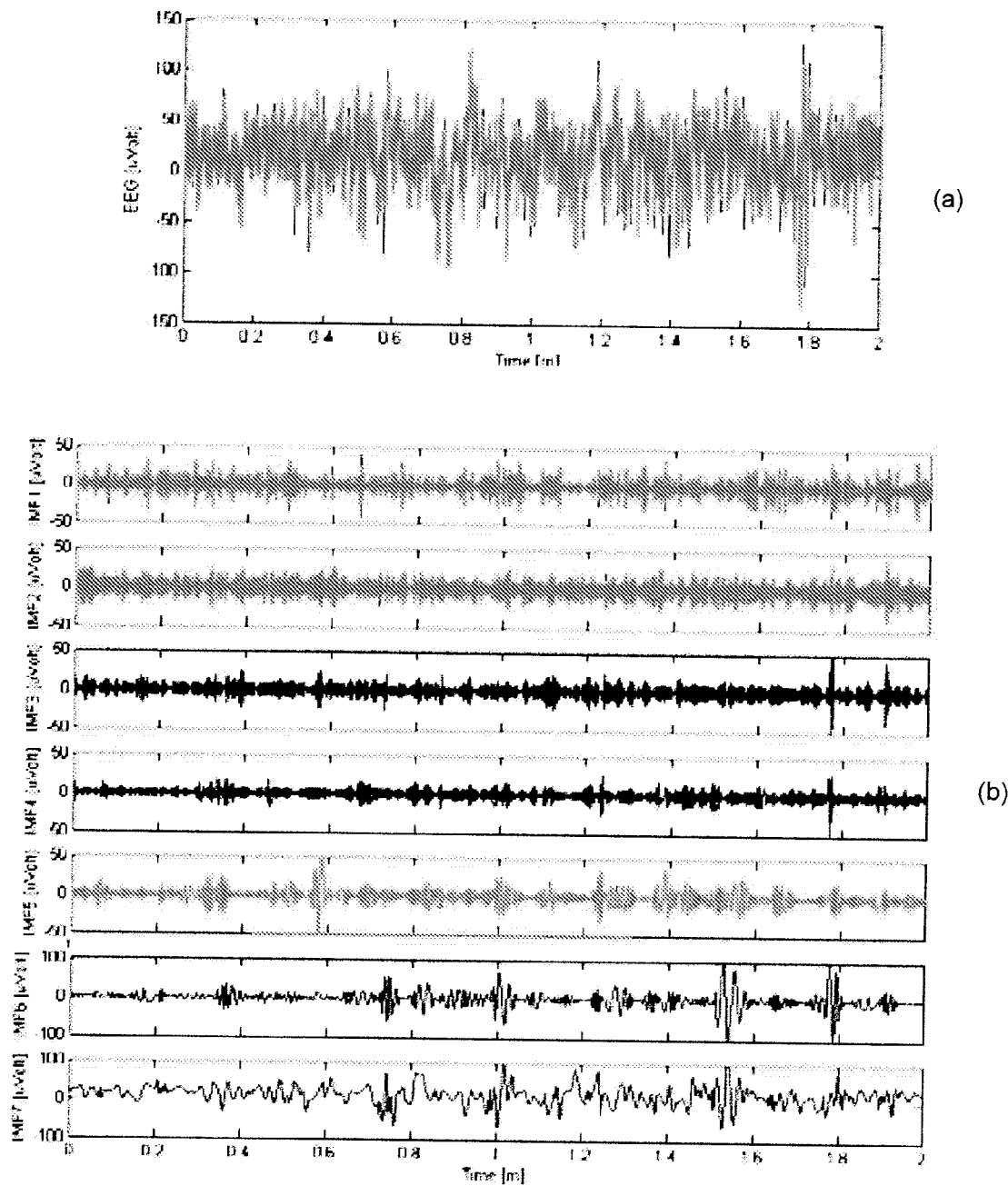
FIG. 10 illustrates an empirical mode decomposition (EMD) used to extract the intrinsic modes of signal oscillation that comprise a time series, including (a) a 2-minute segment of EEG collected from the frontal area (Fp1-Fpz) during infusion of propofol, and (b) the intrinsic mode functions (IMFs) extracted from the 2-minute EEG segment in (a) using the EMD method, according to an exemplary embodiment.

Following the EMD algorithm and using the stopping criterion discussed above, 7 IMFs were obtained from the electroencephalogram time series during infusion of propofol, illustrated in FIG. 10.

Figure 11:
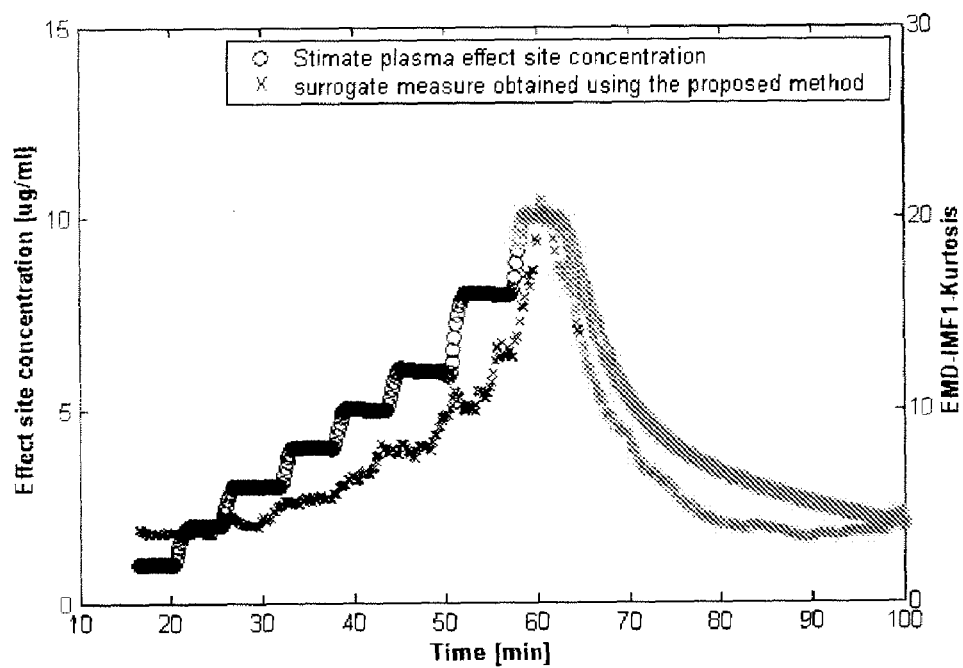
FIG. 11 illustrates changes in gaussianity of the high frequency IMF component of the EEG (IMF1) with drug infusion: Fourth-moment statistic (Kurtosis) may be used to quantify the probability distribution of a time-series, where Kurtosis value equal to 3 may represent a gaussian distribution; Kurtosis value greater than 3 may represent a super-gaussian distribution. Estimated plasma effect site concentration obtained from the infusion pump and a surrogate measure obtained using fourth-moment statistic analysis of the EEG-first intrinsic mode function (IMF1) are shown.
Figure 12:
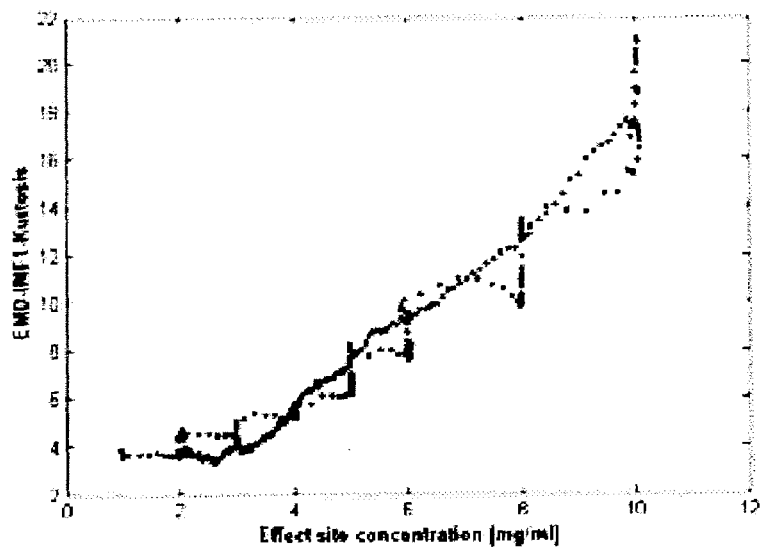
FIG. 12 illustrates the relationship of Kurtosis of IMF1 versus estimated plasma effect site concentration from the infusion pump, for volunteer in FIG. 11. With increasing infusion of the anesthetic, Kurtosis of the EEG-IMF1 increases proportionally. Similarly, a proportional decrease is observed during the recovery phase.

The quantification of the gaussianity changes in the IMF-high frequency, component IMF1, a clear relationship with the estimated plasma effect site concentration obtained from the infusion pump was found as illustrated in FIG. 11. This proportional relationship is maintained during drug infusion, onset, and during recovery time as illustrated in FIG. 12.

Figure 13:
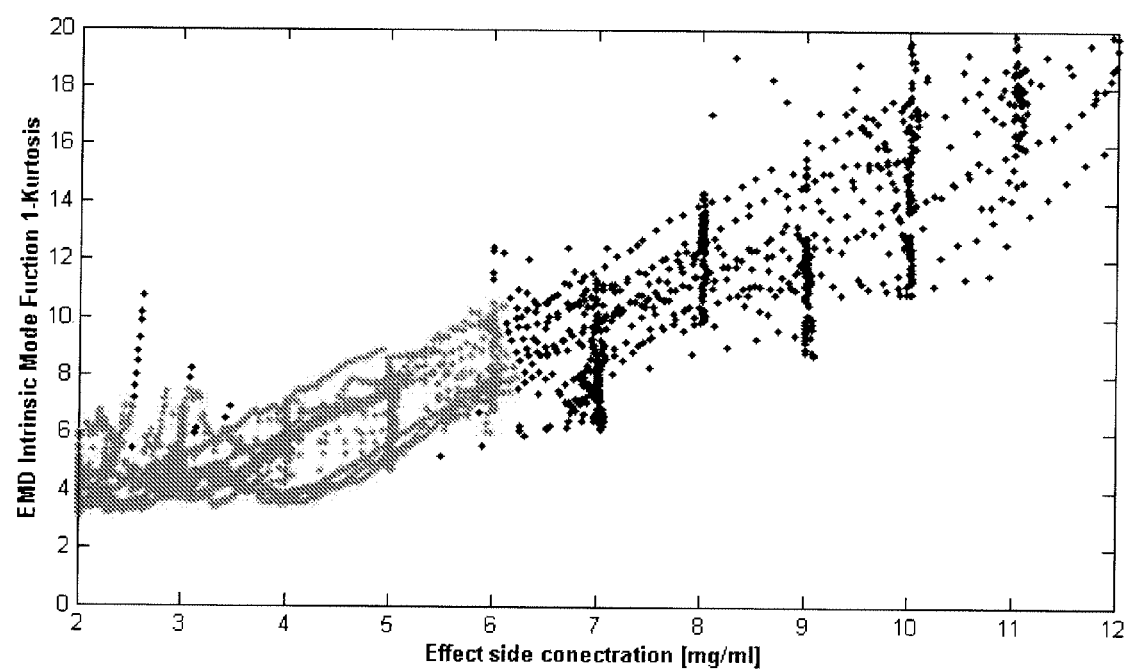
FIG. 13 illustrates the relationship of Kurtosis of IMF1 versus estimated plasma effect site concentration from the infusion pump, for all volunteers. The estimated plasma effect site concentration, obtained from the infusion pump, and the surrogate measure ($K_{EEG-IMF1}$) obtained using the method show a proportional relationship for EEG analyzed from all volunteers, during both onset of and recovery from anesthetic administration.

From 11 volunteers, from a group of 12, the same relationship, between estimate plasma effect side concentration and the changes in the gaussianity of the IMF1, was consistent as illustrated in FIG. 13. The surrogate plasma effect site concentration, estimated with the method, present a high correlation (r=9.23 (0.072), mean(sd)), with the estimated plasma effect site concentration obtained from the infusion pump.

Anesthesia may be administered orally or intravenously in the operating room (OR) and intensive care unit (ICU). In either case, pharmacokinetic and pharmacodynamic models may be used to derive estimates of the actual drug concentration in the body. Further, it is difficult to characterize the plasma effect site concentration of orally administered drugs because the absorption and metabolism mechanisms are not clearly understood. A direct surrogate measure of the actual drug concentration, derived from physiological signals, would be useful for both methods of drug administration.

In this investigation, our analysis revealed a very close relationship between Kurtosis of the first intrinsic mode function of the frontal EEG signals, collected during target-controlled propofol infusion, and the predicted plasma effect site concentration obtained from the infusion pump. Only gaussianity changes of the high frequency INF was analyzed as previous literature suggests a close relationship between consciousness and high frequency behavior of the EEG. Further analysis on the other INFs could reveal deeper insight into neural mechanisms during anesthesia.

An exemplary method comprises empirical mode decomposition followed by fourth-moment statistical analysis of the first intrinsic mode function. These operations may be performed in real-time to provide a surrogate measure of plasma drug concentration that can be used in the OR or ICU. This exemplary method uses the first IMF and does not require all other IMFs to be derived. As a result, the procedure requires fewer computational resources and can be easily used to monitor drug concentrations in real-time.

Our analysis indicates that gaussianity changes of the first IMF closely follow drug characteristics in the body. However, our investigation is limited to target-controlled infusion of propofol in 12 healthy volunteers. We expect that further research will confirm and extend these findings.

Results show linear relationships between the estimated plasma effect site concentration, derived from the infusion pump, and the results from this method. This method may be used in real time during administration of anesthetic in the operating room (OR) or intensive unit care (ICU).

The results from these analyses confirm the ability of entropy indicators to track changes in underlying CNS activity and support that specific montage configurations may be necessary to determine cortical depression that occurs at different locations throughout the CNS as it transitions between different states. The use of computer-controlled delivery of sedatives and analgesics provides a controlled experimental method to change the underlying dynamics of the CNS. Combining these methods will allow us to develop spatial and temporal models of changing CNS.

By considering the surface EEG as a reflection of a dynamic interacting system of cortical and subcortical units that behave independently and in concert, non-linear quantitative methods may be applied to characterize the behavior of this network under perturbed conditions.

While the systems and methods have been described in certain embodiments, these embodiments can be further modified within the spirit and scope of this disclosure. This application is therefore intended to cover any variations, uses, or adaptations of the system and method using its general principles. Further, this application is intended to cover such departures from the present disclosure as come within known or customary practice in the art to which this method pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein.

What is claimed is:

1. A method of indicating a subject's reaction to different agents administered to induce anesthesia, comprising:
receiving first electrical signals from a first set of electrodes and second electrical signals from a second set of electrodes, wherein the first set of electrodes is located on a first region of a head of a subject and the second set of electrodes is located on a second region of the head of the subject;
processing, with a processing circuit of an electroencephalogram monitor, the first electrical signals and the second electrical signals to identify a first reaction of the subject to a first agent;
processing the first electrical signals and the second electrical signals to identify a second reaction of the subject to a second agent; and
determining an anesthetic state of the subject based on the identified first reaction and the identified second reaction.

2. The method of claim 1, wherein the first region comprises a frontal region of the head of the subject and the second region comprises a parieto-temporal region of the head of the subject.

3. The method of claim 2, wherein the first agent is a sedative and the second agent is an analgesic.

4. The method of claim 1, wherein the processing comprises applying a non-linear analysis method to at least the first electrical signals from the first set of electrodes.

5. The method of claim 4, wherein the non-linear analysis method comprises an approximate entropy method.

6. The method of claim 5, wherein the approximate entropy method comprises:
defining a neighborhood of data points; and reducing data points to be processed by excluding data points beyond the neighborhood of data points from the processing.

7. The method of claim 1, wherein the processing comprises applying a gaussianity indicator to at least the first electrical signals to detect bursts in the first electrical signals.

8. The method of claim 1, wherein the processing comprises empirical mode decomposition.

9. The method of claim 1, wherein the processing comprises processing in the time domain only.

10. The method of claim 1, wherein the first reaction and the second reaction are identified independent of previous reactions of the subject to the first agent and the second agent.

* * * * *